(12) United States Patent
Tass et al.

(10) Patent No.: US 8,825,167 B2
(45) Date of Patent: Sep. 2, 2014

(54) DEVICE AND METHOD FOR AUDITORY STIMULATION

(71) Applicants: Forschungszentrum Juelich GmbH, Juelich (DE); ANM Adaptive Neuromodulation GmbH, Juelich (DE); Universitaet Zu Koeln, Cologne (DE)

(72) Inventors: Peter A. Tass, Munich (DE); Hans-Joachim Freund, Ratingen (DE); Oleksandr Popovych, Dueren (DE); Birgit Utako Barnikol, Titz (DE); Joel Niederhauser, Basel (DE); Jean-Christophe Roulet, Ligniéres (CH); Urban Schnell, Muenchenbuchsee (CH)

(73) Assignees: Forschungszentrum Juelich GmbH, Juelich (DE); ANM Adaptive Neuromodulation GmbH, Juelich (DE); Universitaet Zu Koeln, Cologne (DE)

( * ) Notice: Subject to any disclaimer, the term of this patent is extended or adjusted under 35 U.S.C. 154(b) by 0 days.

(21) Appl. No.: 13/796,422

(22) Filed: Mar. 12, 2013

(65) Prior Publication Data
US 2013/0190663 A1 Jul. 25, 2013

Related U.S. Application Data

(63) Continuation of application No. 12/884,557, filed on Sep. 17, 2010, now Pat. No. 8,423,144, which is a continuation of application No. PCT/DE2009/000399, filed on Mar. 20, 2009.

(30) Foreign Application Priority Data

Mar. 20, 2008 (DE) .......................... 10 2008 015 259

(51) Int. Cl.
*A61N 1/18* (2006.01)
*A61N 1/36* (2006.01)
*A61B 5/00* (2006.01)
*A61F 11/00* (2006.01)
*A61M 21/00* (2006.01)
*A61H 1/00* (2006.01)

(52) U.S. Cl.
CPC ................. *A61B 5/486* (2013.01); *A61F 11/00* (2013.01); *A61M 21/00* (2013.01); *A61H 1/00* (2013.01); *A61M 2021/0027* (2013.01)
USPC ............................................... 607/45; 607/46

(58) Field of Classification Search
USPC ...................................................... 607/45–46
See application file for complete search history.

(56) References Cited

U.S. PATENT DOCUMENTS

| 7,166,070 B2 | 1/2007 | Lawlis et al. |
| 7,354,395 B2 | 4/2008 | Lawlis et al. |

(Continued)

FOREIGN PATENT DOCUMENTS

| DE | 102 33 960 A1 | 2/2004 |
| JP | 10-512767 A | 12/1998 |

(Continued)

OTHER PUBLICATIONS

Scott Makeig et al.; "Mining event-related brain dynamics"; *TRENDS in Cognitive Sciences*, vol. 8 No. 5 May 2004.

(Continued)

*Primary Examiner* — Carl H Layno
*Assistant Examiner* — Jon Eric C Morales
(74) *Attorney, Agent, or Firm* — Dickstein Shapiro LLP

(57) ABSTRACT

A device and method for desynchronizing a patient's neuronal brain activity involving a neuron population firing in a pathologically synchronized manner. The device includes a stimulation unit configured to generate an acoustic stimulation signal to stimulate the neuron population when the acoustic stimulation signal is aurally received by the patient. Furthermore, the acoustic stimulation signal has a first frequency and a second frequency, with the first frequency provided to reset the phase of the neuronal brain activity in a first sub-population of the stimulated neuron population, and the second frequency provided to reset the phase of the neuronal brain activity in a second sub-population of the stimulated neuron population.

12 Claims, 10 Drawing Sheets

(56) References Cited

U.S. PATENT DOCUMENTS

| | | | |
|---|---|---|---|
| 7,917,221 B2* | 3/2011 | Tass | 607/45 |
| 8,423,144 B2* | 4/2013 | Tass et al. | 607/45 |
| 2005/0049452 A1 | 3/2005 | Lawlis et al. | |
| 2005/0234290 A1 | 10/2005 | Kwon et al. | |
| 2006/0020161 A1 | 1/2006 | Mageras et al. | |
| 2006/0047324 A1 | 3/2006 | Tass | |
| 2006/0206175 A1 | 9/2006 | Fernandez Tournier et al. | |

FOREIGN PATENT DOCUMENTS

| | | |
|---|---|---|
| WO | WO-2004/098690 A1 | 11/2004 |
| WO | WO-2006/126956 A2 | 11/2006 |

OTHER PUBLICATIONS

M.E. Brandt; "Visual and auditory evoked phase resetting of the alpha EEG"; International Journal of Psychophysiology 26 (1997), pp. 285-298.

P. Sauseng et al.; "Are Event-Related Potential Components Generated by Phase Resetting of Brain Oscillations? A Critical Discussion"; *Neuroscience* 146 (2007), pp. 1435-1444.

Peter Lakatos et al.; "The Leading Sense: Supramodal Control of Neurophysiological Context by Attention"; Neuron 64, Nov. 12, 2009, pp. 419-430.

B. Ross et al.; "Stimulus Induced Desynchronization of Human Auditory 40-Hz Steady-State Responses"; *Journal of Neurophysiology* 94, Aug. 17, 2005, pp. 4082-4093.

Werner Muehlnickel et al.; "Reorganization of auditory cortex in tinnitus"; Proc. Natl. Acad. Sci USA, vol. 95, Aug. 1998, pp. 10340-10343.

Dave R.M. Langers et al.; "Representation of lateralization and tonotopy in primary versus secondary human auditory cortex"; NeuroImage 34 (2007), pp. 264-273.

Deniz Bilecen et al.; "Tonotopic organization of the human auditory cortex as detected by BOLD-FMRI"; Hearing Research 126 1998, pp. 19-27.

\* cited by examiner

DEVICE AND METHOD FOR AUDITORY STIMULATION

CROSS REFERENCE TO RELATED APPLICATIONS

The present application is a continuation of U.S. application Ser. No. 12/884,557, filed Sep. 17, 2010, now U.S. Pat. No. 8,423,144 which claims priority to International Application No. PCT/DE2009/000399, filed Mar. 20, 2009, which claims priority to German Application No. 10 2008 015 259.5, filed Mar. 20, 2008, the entire contents of each of which are incorporated herein by reference.

BACKGROUND

There are excessively strong neuronal activity synchronization procedures in the brain in a number of neurological and psychiatric diseases and these have a very strong negative influence on the cerebral function. Tinnitus is such a disease Tinnitus refers to a sound in the ear, mostly in the form of a high-pitched tone, but occasionally also having a knocking, pulsing or beating character. It is a widespread disease in the form of disturbing sensations that are of an agonizing nature for many patients. Currently available therapy methods for such diseases include pharmacotherapy, deep brain stimulation and the like.

SUMMARY

The present application is directed to a device and method for desynchronizing a patient's neuronal brain activity involving a neuron population firing in a pathologically synchronized manner. The device includes a stimulation unit configured to generate an acoustic stimulation signal to stimulate the neuron population when the acoustic stimulation signal is aurally received by the patient. Furthermore, the acoustic stimulation signal has a first frequency and a second frequency, with the first frequency provided to reset the phase of the neuronal brain activity in a first sub-population of the stimulated neuron population, and the second frequency provided to reset the phase of the neuronal brain activity in a second sub-population of the stimulated neuron population.

In another aspect of the present application, a device is provided for desynchronizing a patient's neuronal brain activity involving a neuron population firing in a pathologically synchronized manner. In this aspect, the device includes a stimulation unit to generate an acoustic stimulation signal to stimulate the neuron population when the acoustic stimulation signal is aurally received by the patient; a measurement unit to record a measurement signal on a patient, which measurement signal reproduces the neuronal activity in the auditory cortex of the patient or a region connected thereto; and a control unit to actuate the stimulation unit based on the measurement signal such that the stimulation unit converts the measurement signal into the acoustic stimulation signal.

In further aspect of the present application, a method is provided for desynchronizing a patient's neuronal brain activity involving a neuron population firing in a pathologically synchronized manner, the method including generating an acoustic stimulation signal to stimulate the neuron population when the acoustic stimulation signal is aurally received by the patient, the acoustic stimulation signal having at least a first frequency and a second frequency; setting the first frequency to reset the phase of the neuronal brain activity in a first sub-population of the stimulated neuron population; and setting the second frequency to reset the phase of the neuronal activity in a second sub-population of the stimulated neuron population.

In yet a further aspect of the application, a method is provided for desynchronizing a patient's neuronal brain activity involving a neuron population firing in a pathologically synchronized manner. In this aspect, the method includes recording a measurement signal on a patient, which measurement signal reproduces the neuronal activity in the auditory cortex or a region connected thereto; converting the measurement signal into an acoustic stimulation signal; and generating the acoustic stimulation signal to stimulate the neuron population when the acoustic stimulation signal is aurally received by the patient.

DETAILED DESCRIPTION

Figure 1:
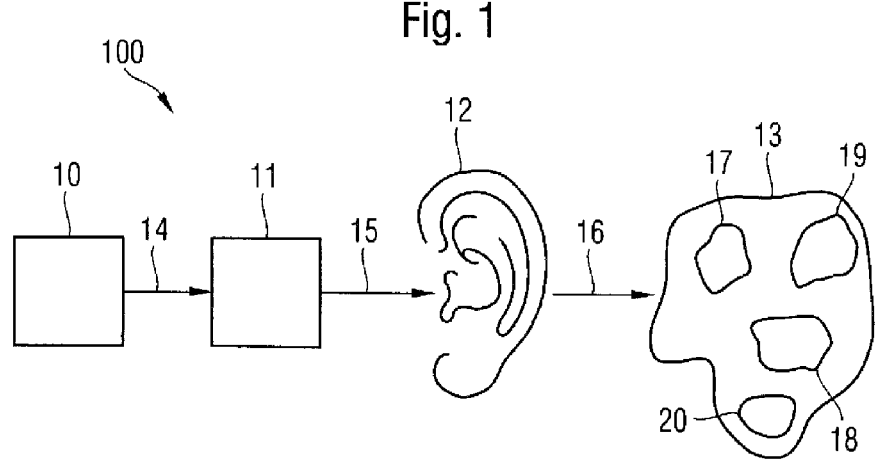
FIG. 1 shows a schematic illustration of a device 100 as per an exemplary embodiment.

FIG. 1 illustrates in a schematic fashion a device 100, which consists of a control unit 10 and a stimulation unit 11 connected to the control unit 10. FIG. 1 furthermore illustrates an ear 12 of a patient and the auditory cortex 13 in the brain of the patient in a schematic fashion.

The stimulation unit 11 is actuated by the control unit 10 by means of one or more control signals 14 during the operation of the device 100, and the stimulation unit 11 generates one or more acoustic stimulation signals 15 with the aid of the control signal 14. The frequency spectrum of the acoustic stimulation signal 15 may lie completely or partly in the range audible to a human. The acoustic stimulation signal 15 is taken in by the patient by one or both ears 12 and is transmitted to neuron populations in the brain via the cochlear nerve or nerves 16. The acoustic stimulation signal 15 is developed such that it stimulates neuron populations in the auditory cortex 13. At least a first frequency $f_1$ and a second frequency $f_2$ are present in the frequency spectrum of the acoustic stimulation signal 15. The acoustic stimulation signal 15 can furthermore contain additional frequencies or frequency mixtures; in the exemplary embodiment shown in FIG. 2, these are a third frequency $f_3$ and a fourth frequency $f_4$.

The device 100 can be used in particular for treating neurological or psychiatric diseases, such as tinnitus, migraine, headaches of different form and genesis (e.g. cluster headache), trigeminal neuralgia, sleep disorders, neuralgias and headaches in the case of neuroborreliosis, attention deficit syndrome (ADS), attention deficit hyperactivity syndrome (ADHS), neuroses, compulsion neuroses, depressions, mania, schizophrenia, tumors, arrhythmias, addiction diseases, bruxism (nocturnal teeth grinding), eating disorders, and the like.

The aforementioned diseases can be caused by a disorder in the bioelectric communication of neural networks connected in specific circuits. Herein, a neuron population continuously generates pathological neuronal activity and possibly a pathological connectivity (network structure) associated therewith. In the process, a large number of neurons form action potentials at the same time, i.e. the involved neurons fire in an overly synchronous fashion. Additionally, the sick neuron population exhibits an oscillatory neuronal activity, i.e. the neurons fire rhythmically. In the case of the aforementioned diseases, the mean frequency of the pathological rhythmic activity of the affected neural networks lies approximately in the range between 1 and 30 Hz, but it can also lie outside of this range. The neurons fire qualitatively differently in healthy humans, e.g. in an uncontrolled fashion.

The acoustic stimulation signal 15 generated by the stimulation unit 11 is converted into nerve impulses in the inner ear and transmitted to the auditory cortex 13 via the cochlear nerve 16. The tonotopic arrangement of the auditory cortex 13 means that a particular part of the auditory cortex 13 is activated in the case of the acoustic stimulation of the inner ear with a particular frequency. The tonotopic arrangement of the auditory cortex is described, for example, in the following articles: "Tonotopic organization of the human auditory cortex as detected by BOLD-FMRI" by D. Bilecen, K. Scheffler, N. Schmid, K. Tschopp and J. Seelig (published in Hearing Research 126, 1998, pages 19 to 27), "Representation of lateralization and tonotopy in primary versus secondary human auditory cortex" by D. R. M. Langers, W. H. Backes and P. van Dijk (published in NeuroImage 34, 2007, pages 264 to 273) and "Reorganization of auditory cortex in tinnitus" by W. Mühlnickel, T. Elbert, E. Taub and H. Flor (published in Proc. Natl. Acad. Sci. USA 95, 1998, pages 10340 to 10343).

In the example as per FIG. 1, the acoustic stimulation signal 15 is developed such that it stimulates a neuron population in the auditory cortex 13 with a pathologically synchronous and oscillatory activity. Before the stimulation is initiated, this neuron population can at least be thought of being subdivided into various sub-populations, inter alia the sub-populations 17, 18, 19 and 20 shown in FIG. 1. Before the stimulation is initiated, the neurons of all sub-populations 17 to 20 for the most part fire synchronously and on average with the same pathological frequency. Due to the tonotopic organization of the auditory cortex 13, the first sub-population 17 is stimulated by means of the first frequency $f_1$, the second sub-population 18 is stimulated by means of the second frequency $f_2$, the third sub-population 19 is stimulated by means of the third frequency $f_3$ and the fourth sub-population 20 is stimulated by means of the fourth frequency $f_4$. The stimulation by the acoustic stimulation signal 15 brings about a resetting, a so-called reset, of the phase of the neuronal activity in the stimulated neurons in the respective sub-populations 17 to 20. The reset sets the phase of the stimulated neurons to a certain phase value, e.g. 0°, independently of the current phase value. Hence the phase of the neuronal activity of the pathological sub-populations 17 to 20 is controlled by means of a targeted stimulation.

The pathological neuron population can be stimulated in a targeted fashion at the different sites 17 to 20 as a result of the tonotopic arrangement of the auditory cortex 13 and the plurality of frequencies $f_1$ to $f_4$ contained in the acoustic stimulation signal 15. This affords the possibility of resetting the phase of the neuronal activity of the pathological neuron population at different times at the different stimulation sites 17 to 20 by applying the frequencies $f_1$ to $f_4$ at different times. As a result, this subdivides the pathological neuron population, the neurons of which were previously active in a synchronous fashion and with the same frequency and phase, into the sub-populations 17 to 20. Within each of the sub-populations 17 to 20, the neurons are still synchronous and also on average still fire with the same pathological frequency, but each of the sub-populations 17 to 20 has the phase in respect of its neuronal activity that was imposed on it by the stimulation stimulus with the associated frequency $f_1$ to $f_4$.

Due to the pathological interaction between the neurons, the state with at least two sub-populations, which state was generated by the stimulation, is unstable and the entire neuron population quickly approaches a state of complete desynchronization, in which the neurons fire in an uncorrelated fashion. The desired state, i.e. the complete desynchronization, thus is not available immediately after the application of the acoustic stimulation signal 15 via the stimulation unit 11, but usually sets in within a few periods or even within less than one period of the pathological activity.

In the type of stimulation described above, the ultimately desired desynchronization is only made possible by the pathologically increased interaction between the neurons. Hereby, a self-organization process is utilized, which is responsible for the pathological synchronization. The same process brings about a desynchronization following a subdivision of an entire population into sub-populations with different phases.

Moreover, the stimulation with the device 100 can obtain a reorganization of the connectivity of the dysfunctional neural networks and so long-lasting therapeutic effects can be brought about, which last significantly longer than the acoustic stimulation.

In order to stimulate the auditory cortex 13 at different sites focally, e.g. the sites or sub-populations 17 to 20 shown in FIG. 1, pure tones of the associated frequencies $f_1$, $f_2$, $f_3$ and $f_4$ have to be dispensed. As a result of the tonotopic arrangement of the auditory cortex 13, different parts of the brain are stimulated by the simultaneous dispensation of the associated various pure tones $f_1$ to $f_4$, i.e. by the superposition of various sinusoidal oscillations. If the four different sites 17 to 20 are intended to be stimulated e.g. at different times, the four different frequencies $f_1$ to $f_4$ are applied at the respective times. This is shown in an exemplary fashion in FIG. 2. Here sinusoidal oscillations at the frequencies $f_1=1000$ Hz, $f_2=800$ Hz, $f_3=600$ Hz and $f_4=400$ Hz are applied successively and as pulses, which leads to a successive focal stimulus at the four different sites 17 to 20 in the auditory cortex 13. The strength of the stimulus of the respective area in the auditory cortex 13 generated by the respective sinusoidal oscillation corresponds to the amplitude of the respective sinusoidal oscillation.

Figure 2:
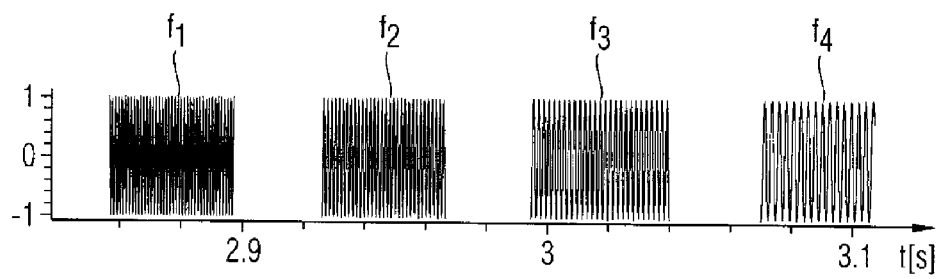
FIG. 2 shows an illustration of sinusoidal oscillations at the frequencies of $f_1$, $f_2$, $f_3$ and $f_4$ as per an exemplary embodiment.
Figure 3:
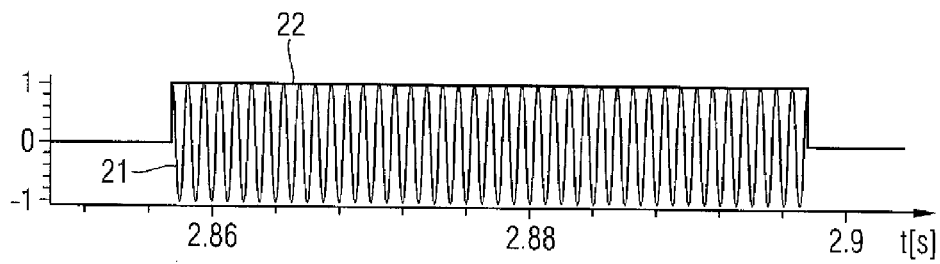
FIG. 3 shows an illustration of a sinusoidal oscillation amplitude-modulated by a rectangular function as per an exemplary embodiment.

The generation of the pulsed sinusoidal oscillations shown in FIG. 2 is illustrated in FIG. 3 in an exemplary fashion. There, a sinusoidal oscillation 21 is multiplied by a rectangular function 22, which can for example assume the values 0 or 1. At the times at which the rectangular function 22 has a value of 0 the associated stimulus is switched off and while the rectangular function 22 equals 1 the stimulus is switched on. The sinusoidal oscillation 21 can be multiplied by any other function instead of the rectangular function 22. As a result this multiplication corresponds to an amplitude modulation of the sinusoidal oscillation 21.

Alternatively, instead of the above-described sinusoidal oscillations, use can also be made of oscillating signals with a different signal form, e.g. rectangular signals oscillating with the corresponding base frequency, for generating the acoustic stimulation signal 15.

Provided that a less focal stimulation that activates relatively large parts of the auditory cortex 13 is intended to be carried out instead of a focal stimulation, frequency mixtures are applied, e.g. in a pulsed fashion, instead of individual frequencies. Using a frequency mixture bounded between a lower frequency $f^{lower}$ and an upper frequency $f^{upper}$ stimulates all those parts of the auditory cortex 13 that are stimulated by the frequencies between $f^{lower}$ and $f^{upper}$ due to the tonotopic arrangement. If, for example, four different, relatively large regions of the auditory cortex 13 are intended to be stimulated at different times, the four associated frequency mixtures with the boundaries $f_j^{lower}$ and $f_j^{upper}$ (j=1, 2, 3, 4) are applied at the desired times.

In the exemplary embodiment, the device 100 can be operated in a so-called "open-loop" mode, in which the control unit 10 actuates the stimulation unit 11 such that the latter generates prescribed acoustic stimulation signals 15 during a defined stimulation time (e.g. over a plurality of hours). Moreover, the device 100 can also be developed to form a device 400 shown in FIG. 4, the latter device constituting a so-called "closed-loop" system. In addition to the components known from FIG. 1, the device 400 also contains a measurement unit 23, which provides one or more measurement signals 24 recorded on the patient and transmits said signals to the control unit 10. In a refinement of this embodiment, provision can be made for the control unit 10 to actuate the stimulation unit 11 on the basis of the measurement signals 24 recorded by the measurement unit 23. The measurement unit 23 can involve non-invasive sensors, such as electroencephalography (EEG) electrodes, magnetoencephalography (MEG) sensors, accelerometers, electromyography (EMG) electrodes and sensors for determining blood pressure, respiration or skin resistance. Furthermore, the measurement unit 23 in the form of one or more sensors can be implanted into the body of the patient. By way of example, epicortical, intracortical or subcutaneous electrodes can be used as invasive sensors. In particular, the measurement unit 23 can be used to measure the physiological activity in the stimulated target region or in a region connected therewith.

Various refinements are feasible in respect of the interaction of the control unit 10 with the measurement unit 23. By way of example, the control unit 10 can perform a demand-driven stimulation. For this, the control unit 10 detects the presence and/or the development of one or more pathological features on the basis of the measurement signals 24 recorded by the measurement unit 23. By way of example, the amplitude or the magnitude of the neuronal activity can be measured and compared to a predetermined threshold. The control unit 10 can be configured such that stimulation of one or more target areas in the auditory cortex is initiated as soon as the prescribed threshold is exceeded. Furthermore, parameters of the acoustic stimulation signals 15, such as the amplitudes of the respective sinusoidal oscillations or the pauses between stimulation sequences, can be set by the control unit 10 on the basis of the development of the pathological features. By way of example, one or more thresholds can be prescribed, and if the amplitude or the magnitude of the measurement signals 24 exceeds or drops below a certain threshold, the control unit 10 varies a particular parameter of the acoustic stimulation signal 15, such as the amplitude of one or more sinusoidal oscillations from which the acoustic stimulation signal 15 is composed.

In a further refinement, provision can be made for the measurement signals 24 recorded by the measurement unit 23 to be converted directly or if need be after one or more processing steps into acoustic stimulation signals 15 and to be applied by the stimulation unit 11. By way of example, the measurement signals 24, amplified and if need be after mathematical combination (e.g. after mixing the measurement signals) with a time delay and linear and/or nonlinear combination steps, can be fed as control signals into the control input of the stimulation unit 11. Herein, the combination mode is selected such that the pathological neuronal activity is counteracted and the acoustic stimulation signals 15 likewise disappear or are at least significantly reduced in strength (amplitude) as the pathological neuronal activity reduces.

Figure 5:
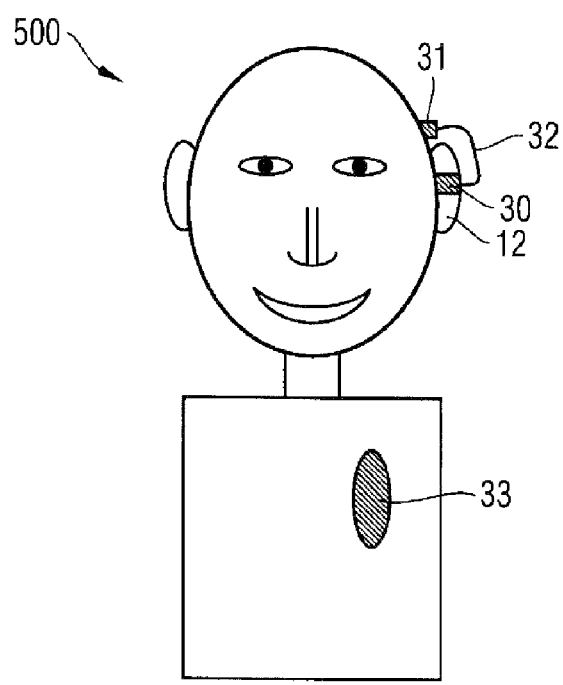
FIG. 5 shows a schematic illustration of a device 500 as per a further exemplary embodiment.

FIG. 5 schematically illustrates a device 500 that constitutes a development of the device 100 shown in FIG. 1. In the exemplary embodiment, there is no need to implant any component of the device 500, and so the entire device 500 is located outside of the body of the patient. Moreover, in this embodiment, the device 500 does not use any signal measured by a sensor for the demand-driven variation of the stimulation. A sound generator (loudspeaker) is used as a stimulation unit 11 in the device 500, which sound generator is surrounded by an earplug 30. The earplug 30 is inserted into the outer auditory canal of an ear 12 of the patient and attached to the ear 12 with or without a holder or another suitable mechanical aid. The control unit 10, which actuates the sound generator, and also a battery or a rechargeable battery for supplying the electrical components of the device 500 with current can be housed in one or more separate units 31. The unit 31 can be connected to the earplug 30 by means of a mechanical fastener, e.g. a holder. A connection cable 32 connects the earplug 30 to the control unit 10 and the battery.

Alternatively, headphones containing the control unit 10 and the battery can also be used instead of the earplug 30. The device 500 can be switched on by the patient by means of an operating unit (e.g. switch-on button and/or control dial), which is attached either to the unit 31 or directly to the earplug 30. The control dial can be used, for example, to set the maximum stimulation strength. In addition to the aforementioned components, the device 500 can comprise a control medium 33, which for example is connected to the control unit 10 in a telemetric fashion (e.g. by radio waves) or by means of a connection cable. In the case of a cabled connection, plug-in connections can be used for connection and disconnection.

Furthermore, the device 500 can also comprise an additional control medium (not illustrated) operable by e.g. the medical practitioner, which control medium is connected to the control unit 10 in a telemetric fashion or by means of a connection cable. In the case of a cabled connection, plug-in connections can be used for connection and disconnection.

Moreover, one or more sensors, such as, EEG electrodes or an accelerometer or the like, can be provided for registering and/or documenting the stimulation success or for the examination by the medical practitioner.

FIGS. 6 to 9 schematically illustrate devices 600, 700, 800 and 900 as developments of the device 400. The devices 600 to 900 in each case comprise a measurement unit 23, by means of which demand-driven control can be performed and/or the measurement signals 24 can be fed back into the stimulation unit 11. In this case, the devices 600 and 700 constitute non-invasive variants, while the devices 800 and 900 are partly implanted into the body of the patient. Like the device 500, the devices 600 to 900 comprise an earplug 30 or headphones with a sound generator.

Figure 6:
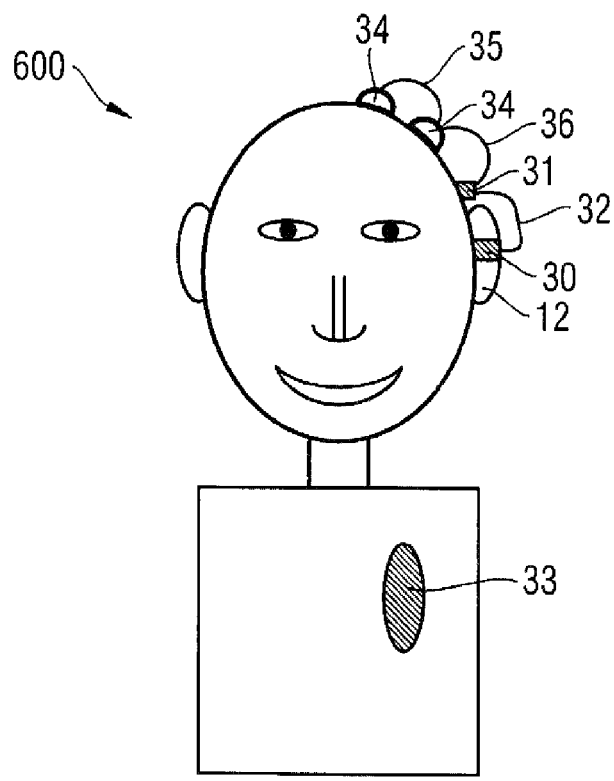
FIG. 6 shows a schematic illustration of a device 600 as per a further exemplary embodiment.

In addition to the above-described components of the device 500, the device 600 illustrated in FIG. 6 comprises epicutaneous, i.e. attached to the skin of the patient, EEG electrodes 34 that are connected to the control unit 10 in the unit 31 via connection cables 35, 36. The control unit 10 amplifies the potential difference measured by means of the EEG electrodes 34 and uses said potential difference for actuating the sound generator in the earplug 30 after an optional linear or nonlinear combination. As an alternative to the connection cables 35, 36, the EEG electrodes 34 can also be connected wirelessly, i.e. telemetrically, to the control unit 10. The advantage of this is that the patient is not impeded by connection cables and can not be caught in obstacles, for example.

Figure 7:
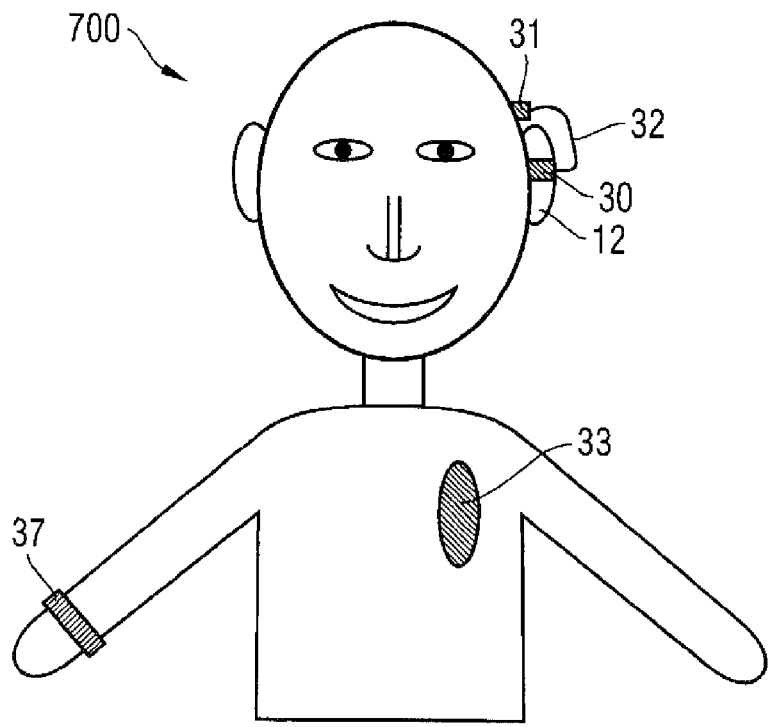
FIG. 7 shows a schematic illustration of a device 700 as per a further exemplary embodiment.

The device 700 illustrated in FIG. 7 has an accelerometer 37 as a measurement unit instead of an EEG electrode. The accelerometer 37 is attached, like a watch, to a limb of the patient that trembles due to disease. The acceleration signals recorded by the accelerometer 37 are amplified in the control unit 10 and are used for actuating the sound generator in the earplug 30 after an optional linear or nonlinear combination. The accelerometer 37 can be connected to the control unit 10 in a telemetric fashion or by means of a connection cable.

Figure 8:
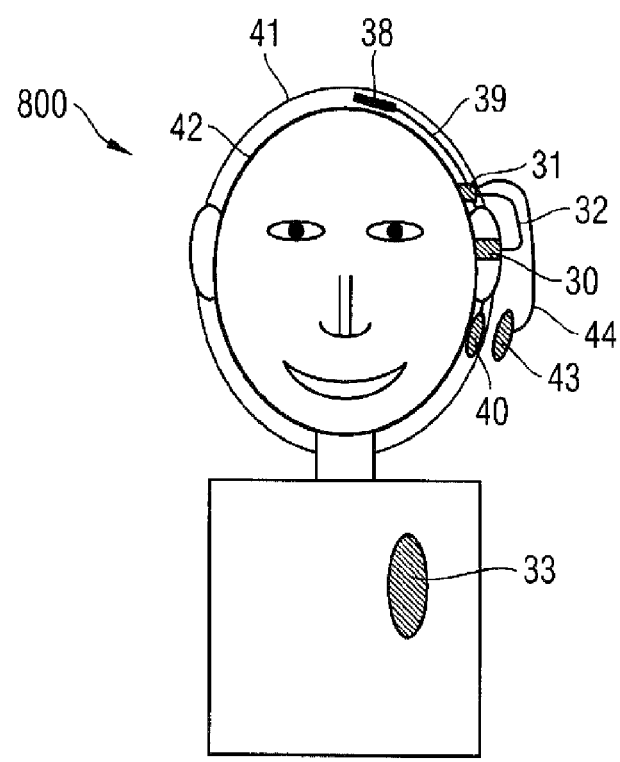
FIG. 8 shows a schematic illustration of a device 800 as per a further exemplary embodiment.

FIG. 8 shows an invasive variant. In the illustrated exemplary embodiment, the device 800 comprises one or more subcutaneously implanted electrodes 38 as a measurement unit, a connection cable 39 and a transmission and reception unit 40, which are implanted into the body of the patient under the scalp 41 and outside of the bony skull 42. Outside of the body of the patient there is a transmission and reception unit 43, which is connected to the unit 31 and the control unit 10 situated therein via a connection cable 44. The measurement signals 24 recorded by the electrode 38 are transmitted to the control unit 10 via the transmission and reception units 40 and 43, which for example are each implemented as a coil and which allow the wireless and bidirectional transmission of signals and electrical power therebetween. The potential differences measured by the electrode 38 are amplified in the control unit 10 and are used for actuating the sound generator integrated into the earplug 30 after an optional linear or nonlinear combination.

Figure 9:
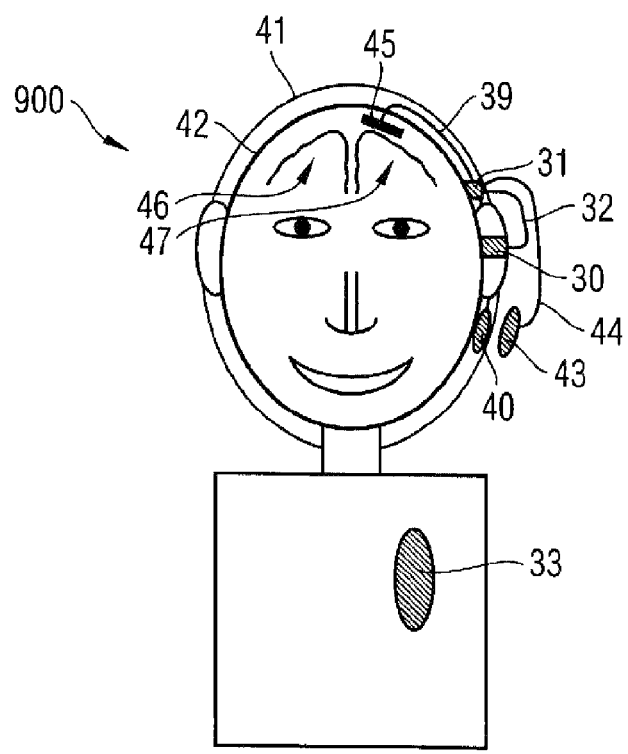
FIG. 9 shows a schematic illustration of a device 900 as per a further exemplary embodiment.

A further invasive variant is illustrated schematically in FIG. 9. One or more epicortically implanted electrodes 45 serve as a measurement unit in the device 900 shown therein. One skilled in the art understand that "epicortical" means "situated on the cerebral cortex." As shown in FIG. 9, the cerebral cortex 46, 47 of both hemispheres is shown schematically for illustrative purposes. The control unit 10 amplifies the potential difference measured by means of the epicortically implanted electrode 45 and uses said potential difference for actuating the sound generator in the earplug 30 after an optional linear or nonlinear combination.

The epicortical electrode 45 shown in FIG. 9 can for example also be replaced by an intracortical electrode (not illustrated).

The measurement signals recorded by the differently developed measurement units 23, i.e. the EEG-electrodes 34, the accelerometer 37 or the electrodes 38 or 45, can be used for feed-back control, as will be described in still more detail further below, and in one embodiment can be fed into the sound generator as actuation signals. Alternatively, demand-driven control can be carried out on the basis of the measurement signals 24. In the case of a stimulation targeted at resetting the neuronal phases of neuron sub-populations, certain parameters of the stimulation method, such as the stimulation strength or the stimulation duration, can be set with the aid of the measurement signals 24. This type of demand-driven control will be explained in still more detail further below in conjunction with FIGS. 10 to 12.

The four frequencies $f_1$ to $f_4$ are intended to be used below to explain in an exemplary fashion as to how a time-offset reset of the phases of the neuronal activity of sub-populations of a pathologically synchronous and oscillatory neuron population can achieve a desynchronization of the entire neuron population. The four frequencies $f_1$ to $f_4$ should merely be understood as exemplary, and it should be understood that any other number of frequencies or frequency mixtures can be used for stimulation purposes. The frequencies $f_1$ to $f_4$ have been selected such that they in each case stimulate particular regions 17 to 20 of the auditory cortex 13. This affords the above-described subdivision of a pathological neuron population into sub-populations 17 to 20. In order for the sub-populations 17 to 20 to have different phases after the stimulation, the frequencies $f_1$ to $f_4$ can for example be applied with a time offset.

Figure 10:
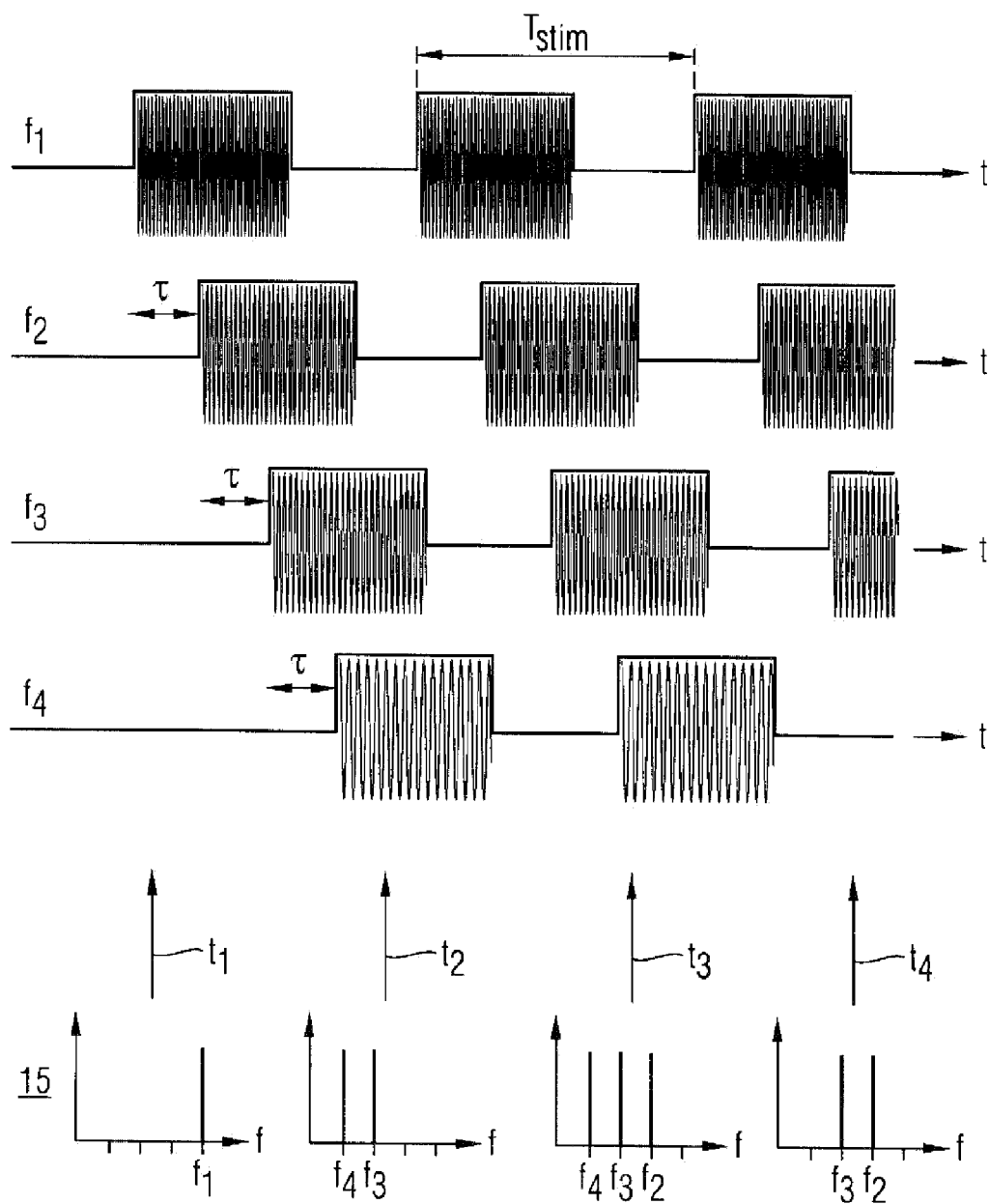
FIG. 10 shows a schematic illustration of an auditory stimulation method as per an exemplary embodiment.

A stimulation method that is suitable for the above-described purposes and can for example be performed by one of the devices 100 to 900 is illustrated schematically in FIG. 10. The upper four rows of FIG. 10 plot, one below the other, four sinusoidal oscillations with frequencies $f_1$, $f_2$, $f_3$ and $f_4$ over time t. The acoustic stimulation signal 15 is formed from the illustrated sinusoidal oscillations. The four sinusoidal oscillations have been multiplied by rectangular functions for generating pulsed sinusoidal oscillations. Each sinusoidal oscillation pulse is repeated periodically with a frequency $f_{stim}$. The frequency $f_{stim}=1/T_{stim}$ preferably lies in the range between 1 and 30 Hz and more particularly in the range between 5 and 20 Hz, but it can also assume smaller or greater values as should be understood to one skilled in the art. Such sequences of pulsed sinusoidal oscillations are suitable for resetting the neuronal phase of the respectively stimulated pathological neuron sub-population 17, 18, 19 or 20 if said oscillations are applied as acoustic stimulation signals 15. Here the phase reset does not necessarily already result after one or a few pulses, but a certain number of the sinusoidal oscillation pulses shown in FIG. 10 may be required to reset the neuronal phase of the respective sub-population 17, 18, 19 or 20.

By way of example, the frequency $f_{stim}$ can lie in the vicinity of the mean frequency of the pathologically rhythmic activity of the target network. In the case of neurological and psychiatric diseases, the mean frequency typically lies in the range between 1 and 30 Hz, but it can also lie outside of this range as noted above. In the case of tinnitus, there is overly synchronous neuronal activity in, for example, the frequency range between 1.5 and 4 Hz. It should be noted herein that the frequency at which the pathological neurons fire synchronously is usually not constant, but can by all means have variations and moreover has individual deviations in each patient.

The mean peak frequency of the pathological rhythmic activity of the patient can for example be determined in order to calculate the frequency $f_{stim}$. This peak frequency can then be used as stimulation frequency $f_{stim}$, or else be varied, for example in a range between $f_{stim}-3$ Hz and $f_{stim}+3$ Hz. However, alternatively it is also possible for a frequency $f_{stim}$ to be selected in the range between 1 and 30 Hz without a preceding measurement and this frequency can for example be varied during the stimulation until the frequency $f_{stim}$ is found, by means of which the best stimulation successes can be obtained. As a further alternative, a known value found in the literature for the respective disease can be used for the stimulation frequency $f_{stim}$. If need be, this value can still be varied until for example optimum stimulation results are obtained.

The duration of a sinusoidal oscillation pulse, i.e. the period of time during which the rectangular function assumes a value of 1 in the present refinement, can for example be $T_{stim}/2$. In this case, the period of time during which the respective frequency contributes to the stimulation and the subsequent stimulation pause have the same length. However, other stimulation durations can also be selected, for example in the range between $T_{stim}/2-T_{stim}/10$ and $T_{stim}/2+T_{stim}/10$. Other stimulation times are also possible, for example, the stimulation duration is $T_{stim}/4$ in the stimulations shown in FIGS. 11 and 12. The stimulation durations can for example be determined experimentally.

According to the refinement shown in FIG. 10, the individual frequencies $f_1$ to $f_4$ are dispensed with a time delay between the individual frequencies $f_1$ to $f_4$. By way of example, the beginning of temporally successive pulses having different frequencies can be offset by a time $\tau$.

In the case where N frequencies are used for the stimulation, the time delay $\tau$ between two respectively successive pulses can for example lie in the vicinity of an N-th of the period $T_{stim}=1/f_{stim}$. In the exemplary embodiment (N=4) shown in FIG. 10, the time delay $\tau$ correspondingly is $T_{stim}/4$. In one embodiment, there can be a certain amount of deviation from the specification that the time delay $\tau$ between two respectively successive sinusoidal oscillation pulses is $T_{stim}/N$. By way of example, there can be a deviation of up to ±10%, ±20% or ±30% from the value $T_{stim}/N$ for the time delay $\tau$. Stimulation successes were still obtained in the case of such a deviation, i.e. a desynchronizing effect could still be observed.

In the exemplary embodiment, the acoustic stimulation signal 15 is formed by superposition of the periodic sinusoidal oscillation pulses with the frequencies $f_1$ to $f_4$. The individual sinusoidal oscillation pulses can in this case for example be combined in a linear or nonlinear fashion. This means that the sinusoidal oscillations with the individual frequencies $f_1$ to $f_4$ need not necessarily be combined with the same amplitudes in order to form the acoustic stimulation signal 15. The frequency spectrum of the acoustic stimulation signal 15 at four different times $t_1$, $t_2$, $t_3$ and $t_4$ is illustrated in the bottom row of FIG. 10 in an exemplary fashion. The frequency spectra illustrated there, more particularly the height and shape of the frequency peaks, should be understood to be merely exemplary and can also have completely different shapes. In detail, the following statements can be gathered from the illustrated frequency spectra: Only the frequency $f_1$ occurs in the acoustic stimulation signal 15 at the time $t_1$. At the time $t_2$, these are the frequencies $f_3$ and $f_4$; at the time $t_3$, these are the frequencies $f_2$ to $f_4$; and at the time $t_4$, these are the frequencies $f_2$ and $f_3$.

According to an alternative refinement, four frequency mixtures with the boundaries $f_j^{lower}$ and $f_j^{upper}$ (j=1, 2, 3, 4) are used instead of the frequencies $f_1$ to $f_4$. There can be any number of frequencies in the frequency mixture between $f_j^{lower}$ and $f_j^{upper}$ in a frequency mixture j.

According to a further alternative refinement, other functions are used instead of the rectangular functions in order to modulate the amplitude of the sinusoidal oscillations, e.g. sinusoidal half-waves with frequencies lower than $f_1$ to $f_4$. By way of example, it is furthermore feasible for triangular pulses to be used as modulation functions. Such a pulse can have a jump-like onset (from 0 to 1) and thereafter decrease to 0, wherein the decrease can for example be given by a linear or exponential function. The modulation function ultimately determines the shape of the envelope of the individual pulses.

Figure 11:
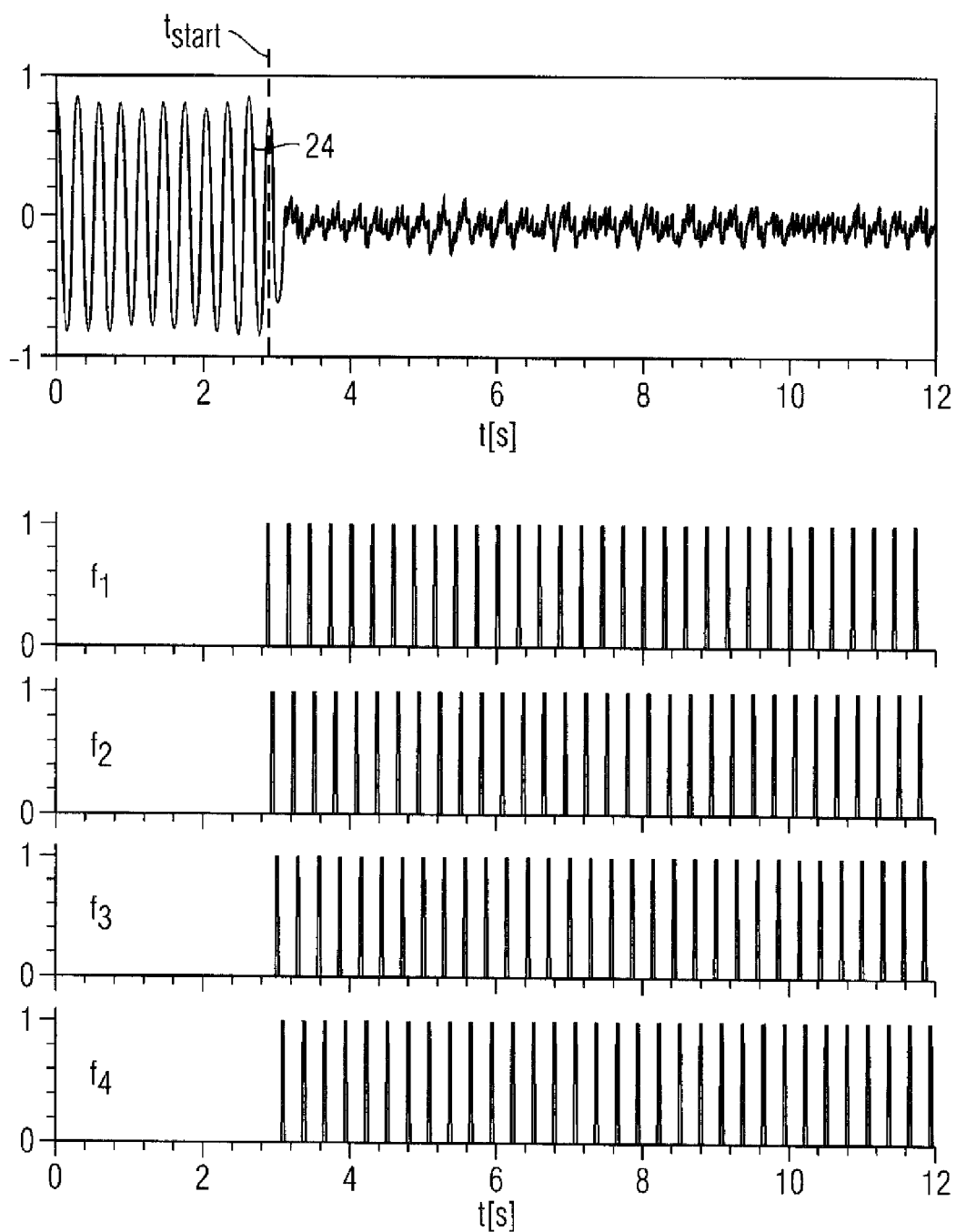
FIG. 11 shows a schematic illustration of a further auditory stimulation method as per an exemplary embodiment.

FIG. 11 illustrates the stimulation shown previously in FIG. 10 over a relatively long period of time. The individual sinusoidal oscillations, with the frequencies $f_1$=1000 Hz, $f_2$=800 Hz, $f_3$=600 Hz and $f_4$=400 Hz, have not been shown in FIG. 11, but only the respective rectangular envelopes. Furthermore, FIG. 11 illustrates a measurement signal 24 recorded by the measurement unit 23 for example, which measurement signal reproduces the neuronal activity in the auditory cortex before and during the stimulation. In the present case, the period $T_{stim}$ is 1/(3.5 Hz)=0.29 s.

As shown in this example, the stimulation is started at the time $t_{start}$. It can be gathered from the measurement signal 24, which has been band-pass filtered in the present example, that the neurons in the auditory cortex have a synchronous and oscillatory activity before the start of the stimulation. The pathologically synchronous neuronal activity in the target area has already been suppressed shortly after the start of the stimulation.

There can be various deviations from the strictly periodic stimulation pattern shown in FIGS. 10 and 11. By way of example, the time delay $\tau$ between two successive sinusoidal oscillation pulses need not necessarily always be of the same magnitude. It should be understood that provision can be made for the time separations between the individual sinusoidal oscillation pulses to be selected such that they differ. Furthermore, the delay times can also be varied during the treatment of a patient. The delay times can also be adjusted in respect of the physiological signal run times.

Furthermore, in one refinement of the exemplary embodiment, pauses can be provided during the application of the acoustic stimulation signal 15, during which pauses there is no stimulation. The pauses can be selected to have any duration and more particularly are an integer multiple of the period $T_{stim}$. The pauses can be held after any number of stimulations. By way of example, a stimulation can be performed over N successive periods of length $T_{stim}$, and there can subsequently be a stimulation pause over M periods of length $T_{stim}$, wherein N and M are small whole numbers, for example in the range between 1 and 15. This scheme can be either continued periodically or modified stochastically and/or deterministically, for example, chaotically.

Figure 12:
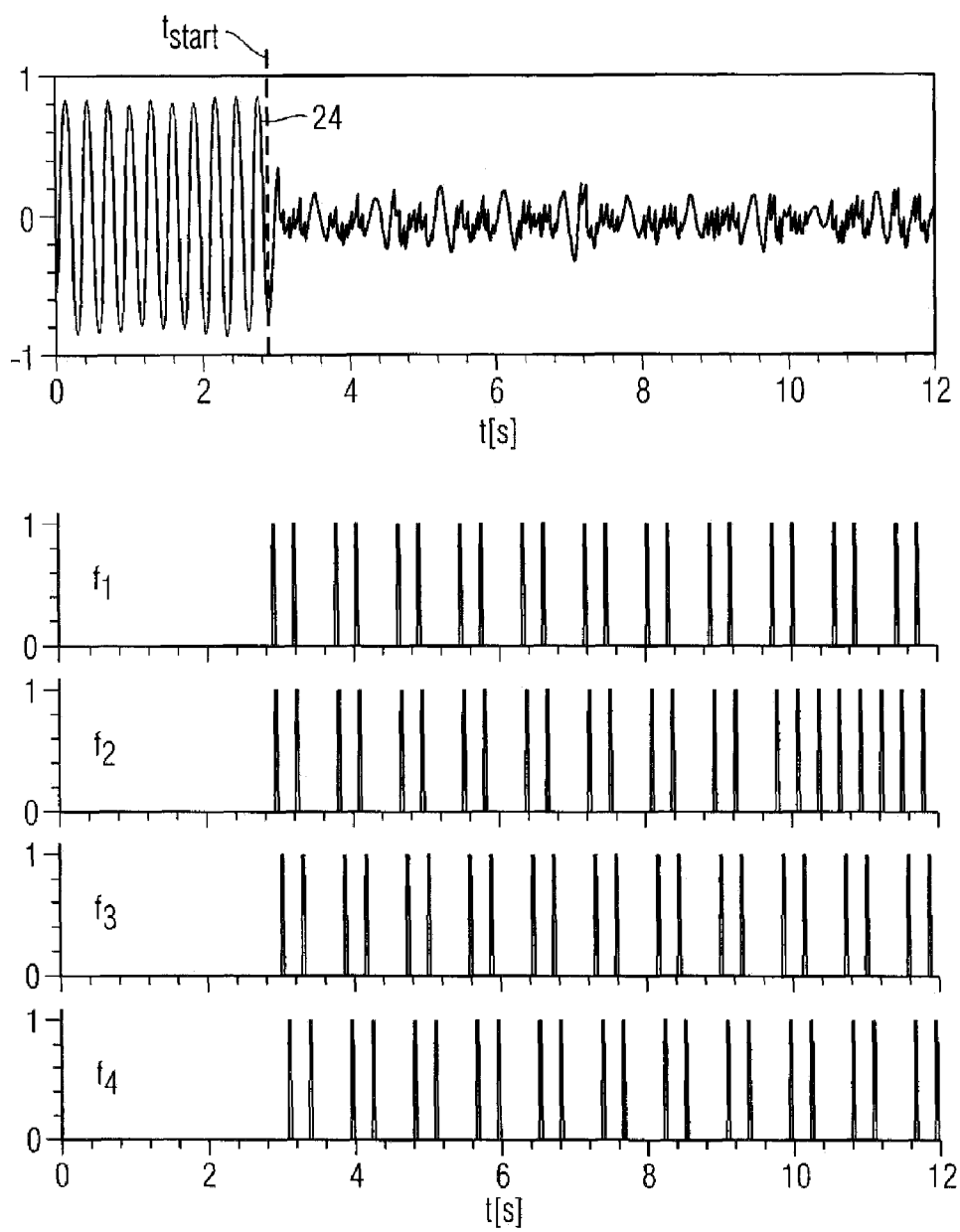
FIG. 12 shows a schematic illustration of a further auditory stimulation method as per an exemplary embodiment.

FIG. 12 shows such a stimulation. Here N=2 and M=1 hold true. Otherwise the stimulation corresponds to the stimulation shown in FIG. 11.

In one refinement, a further option for deviating from the strictly periodic stimulation pattern shown in FIG. 10 consists of stochastic or deterministic or mixed stochastic-deterministic variation of the time separations between successive pulses with a frequency $f_j$ or a frequency mixture with the boundaries $f_j^{lower}$ and $f_j^{upper}$ (j=1, 2, 3, 4).

Additionally, the order in which the involved frequencies $f_j$ or frequency mixtures with the boundaries $f_j^{lower}$ and $f_j^{upper}$ are applied can be varied during each period $T_{stim}$ (or during other time steps). Preferably, this variation can be stochastic or deterministic or mixed stochastic-deterministic.

Furthermore, it is possible for only a certain number of the frequencies $f_t$ or frequency mixtures with the boundaries $f_j^{lower}$ and $f_j^{upper}$ to be applied in each period $T_{stim}$ (or another time interval) and the frequencies $f_t$ or frequency mixtures with the boundaries $f_j^{lower}$ and $f_j^{upper}$ involved in the stimulation can be varied during each time interval. This variation can also be stochastic or deterministic or mixed stochastic-deterministic.

The above-described stimulation signals bring about a reset at different times in the phase of the neuronal activity of the pathological neuron population at the different stimulation sites. This splits the pathological neuron population, the neurons of which were previously active in a synchronous fashion and with the same frequency and phase, into a plurality of sub-populations, which ultimately leads to a desynchronization.

In one embodiment, all stimulation forms described above can also be performed in a "closed-loop" mode. Resetting the phases of the individual sub-populations can for example be linked to a demand-driven control. By way of example, a threshold can be prescribed and if the amplitude of the measurement signal 24 exceeds or drops below the threshold the stimulation can be started or interrupted. Furthermore, certain stimulation parameters, such as the amplitude/strength of the stimulation signals or the duration of the stimulation, can be set on the basis of the amplitude of the measurement signal 24, which can for example be recorded during stimulation pauses. Moreover, it is possible for the frequency $f_{stim}$ to be set or readjusted on the basis of the mean frequency of the (possibly band-pass filtered) measurement signal 24.

Moreover, it is feasible for the stimulation to be started by the patient, for example by means of a telemetric activation. In this case, the patient can activate the stimulation for a prescribed period of time (e.g., 5 minutes) or the patient can independently start and stop the stimulation.

Figure 4:
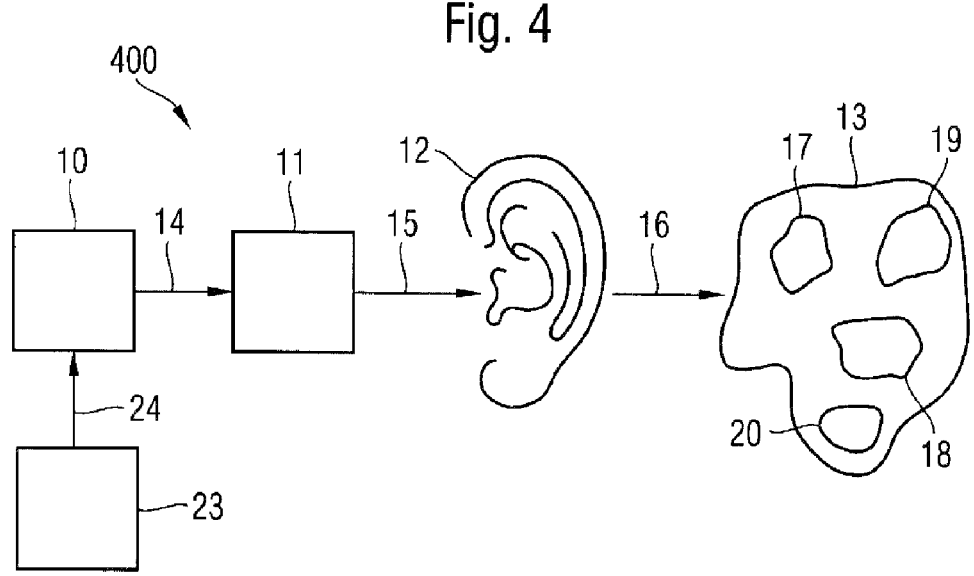
FIG. 4 shows a schematic illustration of a device 400 as per a further exemplary embodiment.

Herein below, further refinements of the "closed-loop" stimulation are described, which can for example be performed by means of the device 400 shown in FIG. 4 or one of the exemplary devices 600 to 900. As already described previously, the measurement signal 24 recorded by the measurement unit 23 can be used to generate a control signal 14, by means of which the stimulation unit 11 is actuated. Here, the measurement signal 24 can be converted directly or if need be after one or more processing steps into the acoustic stimulation signal 15 and can be applied by the stimulation unit 11. Herein, the combination mode can be selected such that the pathological neuronal activity is counteracted and the acoustic stimulation signal 15 likewise disappears or is at least significantly reduced in its strength as the pathological neuronal activity reduces.

In one embodiment, before the measurement signal 24 is fed into the control input of the stimulation unit 11, the measurement signal 24 can be processed in a linear or nonlinear fashion. By way of example, the measurement signal 24 can be filtered and/or amplified and/or acted upon with a time delay and/or mixed with another measurement signal 24. Furthermore, the measurement signal 24 or the processed measurement signal 24 can modulate the amplitude of a sinusoidal oscillation with a frequency in the audible range and the amplitude-modulated sinusoidal oscillation can thereafter be applied as an acoustic stimulation signal 15 or part thereof by means of the sound generator.

Figure 13:
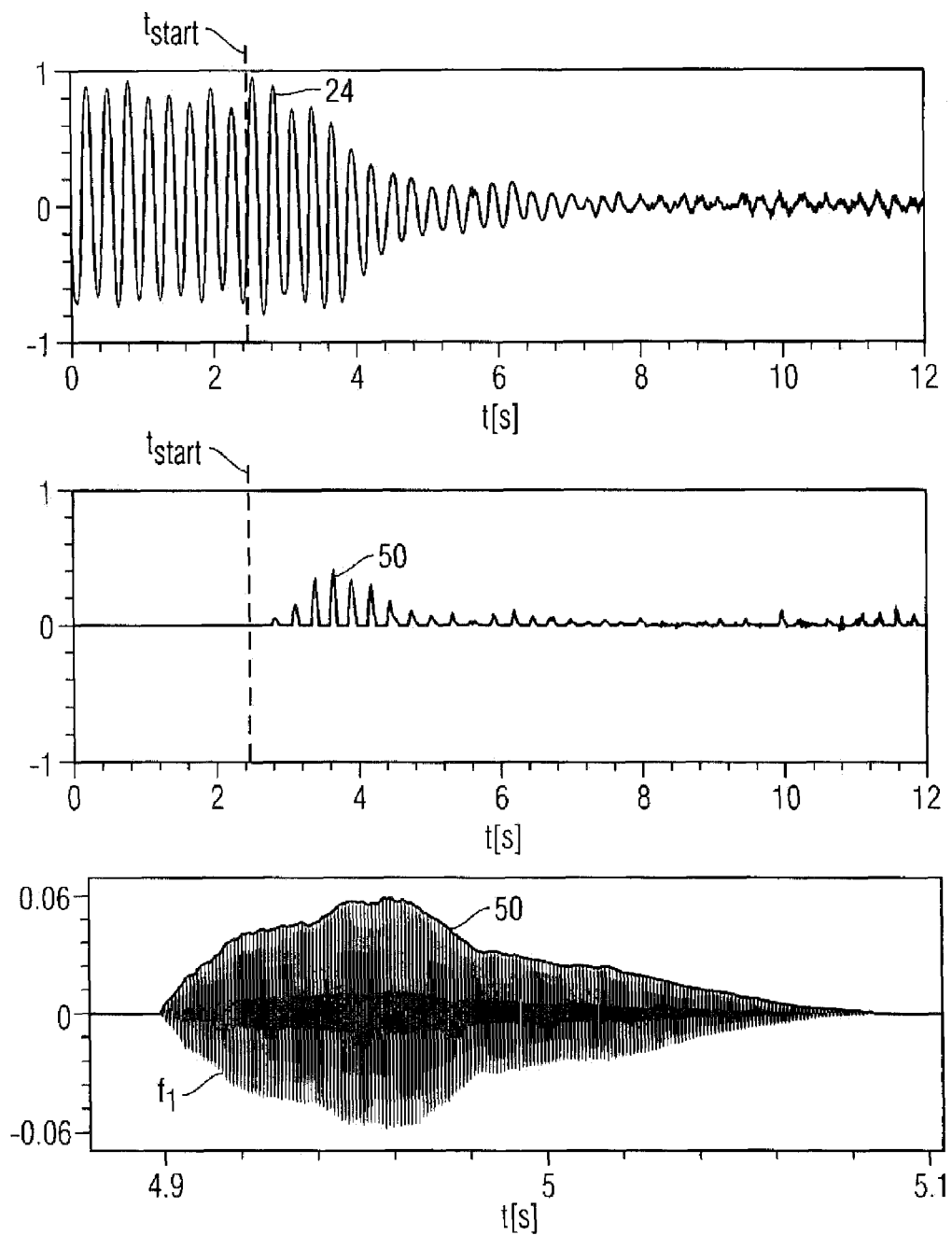
FIG. 13 shows a schematic illustration of a further auditory stimulation method as per an exemplary embodiment.

It should be noted that it is not necessary for the entire measurement signal 24 to be used for modulating the amplitude of a sinusoidal oscillation or another oscillating oscillation. By way of example, provision can be made for only part of the measurement signal 24 or the processed measurement signal 24 to be used for this, for example the part lying above or below a particular threshold. Such an amplitude modulation is illustrated in FIG. 13 in an exemplary fashion. The uppermost graph in FIG. 13 plots the band-pass filtered measurement signal 24 over time t; furthermore, the start time $t_{start}$ of the stimulation is specified. The middle graph illustrates the modulation signal 50 obtained from the measurement signal 24. The measurement signal 24 has been processed in a nonlinear fashion and all negative values of the measurement signal 24 or the processed measurement signal 24 have been set to zero in order to generate the modulation signal 50. Furthermore, the modulation signal 50 has a time delay compared to the measurement signal 24. The half-wave signal 50 obtained in this fashion has subsequently been multiplied with a sinusoidal oscillation at a frequency of $f_1=1000$ Hz. The modulation signal 50 constitutes the envelope of the sinusoidal oscillation, as shown in the lowermost graph of FIG. 13 for a small time interval. The amplitude-modulated sinusoidal oscillation obtained thereby has subsequently been coupled back into the stimulation unit 11 in order to be converted into the acoustic stimulation signal 15 by the sound generator.

Instead of a sinusoidal oscillation with a single frequency, the modulation signal 50 can also be multiplied by any mixture of sinusoidal oscillations (or other oscillations) in the audible frequency range depending on in which sites in the auditory cortex the desynchronization should be brought about.

It can be read out from the profile of the measurement signal 24 illustrated in FIG. 13 that the acoustic nonlinear time-delayed half-wave stimulation leads to a robust suppression of the pathologically synchronous neuronal activity. However, the mechanism of action of this stimulation differs from the mode of operation of the stimulation method shown in e.g. FIG. 10. In the stimulation illustrated in FIG. 13, it is not the phase of the neuronal activity in the respectively stimulated sub-populations that is reset, but the synchronization in the pathologically active neuron population is suppressed by influencing the saturation process of the synchronization.

The following text explains with the aid of an example how a measurement signal 24 obtained by the measurement unit 20 can be subjected to nonlinear processing before it is used as an actuation signal for the stimulation unit 11.

The start point is an equation for the actuation signal S(t):

$$S(t)=K \cdot \overline{Z}^2(t) \cdot \overline{Z}^*(t-\tau). \qquad (1)$$

In equation (1), K is an amplification factor that can be selected in a suitable fashion and $\overline{Z}(t)$ is an average state variable of the measurement signal 24. $\overline{Z}(t)$ is a complex variable and can be represented as follows:

$$\overline{Z}(t)=X(t)+iY(t), \qquad (2)$$

wherein X(t) can correspond to e.g. the neurological measurement signal 24. Since the considered frequencies lie in the vicinity of 10 Hz=1/100 ms=$1/T_\alpha$, the imaginary part Y(t) can be approximated by $X(t-\tau_\alpha)$, wherein for example $\tau_\alpha=T_\alpha/4$ holds true. This results in:

$$S(t)=K \cdot [X(t)+iX(t-\tau_\alpha)]^2 \cdot [X(t-\tau)-iX(t-\tau-\tau_\alpha)]. \qquad (3)$$

Equation (3) can be rewritten as follows:

$$S(t) = K \cdot [X(t)^2 \cdot X(t-\tau) + i2x(t) \cdot X(t-\tau_\alpha) \cdot X(t-\tau) - \quad (4)$$
$$X(t-\tau_\alpha) \cdot X(t-\tau) - iX(t-\tau-\tau_\alpha) \cdot X(t)^2 +$$
$$2X(t) \cdot X(t-\tau_\alpha) \cdot X(t-\tau-\tau_\alpha) + iX(t-\tau-\tau_\alpha) \cdot (t-\tau_\alpha)].$$

The real part of equation (4) is used as the actuation signal for the stimulation unit 11:

$$\text{real}[S(t)] = K \cdot [X(t)^2 X(t-\tau) - X(t-\tau_\alpha) \cdot X(t-\tau) + 2X(t) \cdot X(t-\tau_\alpha) \cdot X(t-\tau-\tau_\alpha)] \quad (5)$$

The auditory cortex can furthermore be stimulated at different sites in a targeted fashion by using the fed-back and possibly further-processed measurement signal 24. In the case of the above-described four different frequencies $f_1$ to $f_4$, the possibly further-processed measurement signal 24 is acted upon by an appropriate time delay and multiplied by the frequencies $f_1$ to $f_4$. Provided that the stimulation is intended to be less focal and over a larger area, four different frequency mixtures with the boundaries $f_j^{lower}$ and $f_j^{upper}$ (j=1, 2, 3, 4) are used instead of the pure sinusoidal oscillations at the frequencies $f_1$ to $f_4$.

Figure 14:
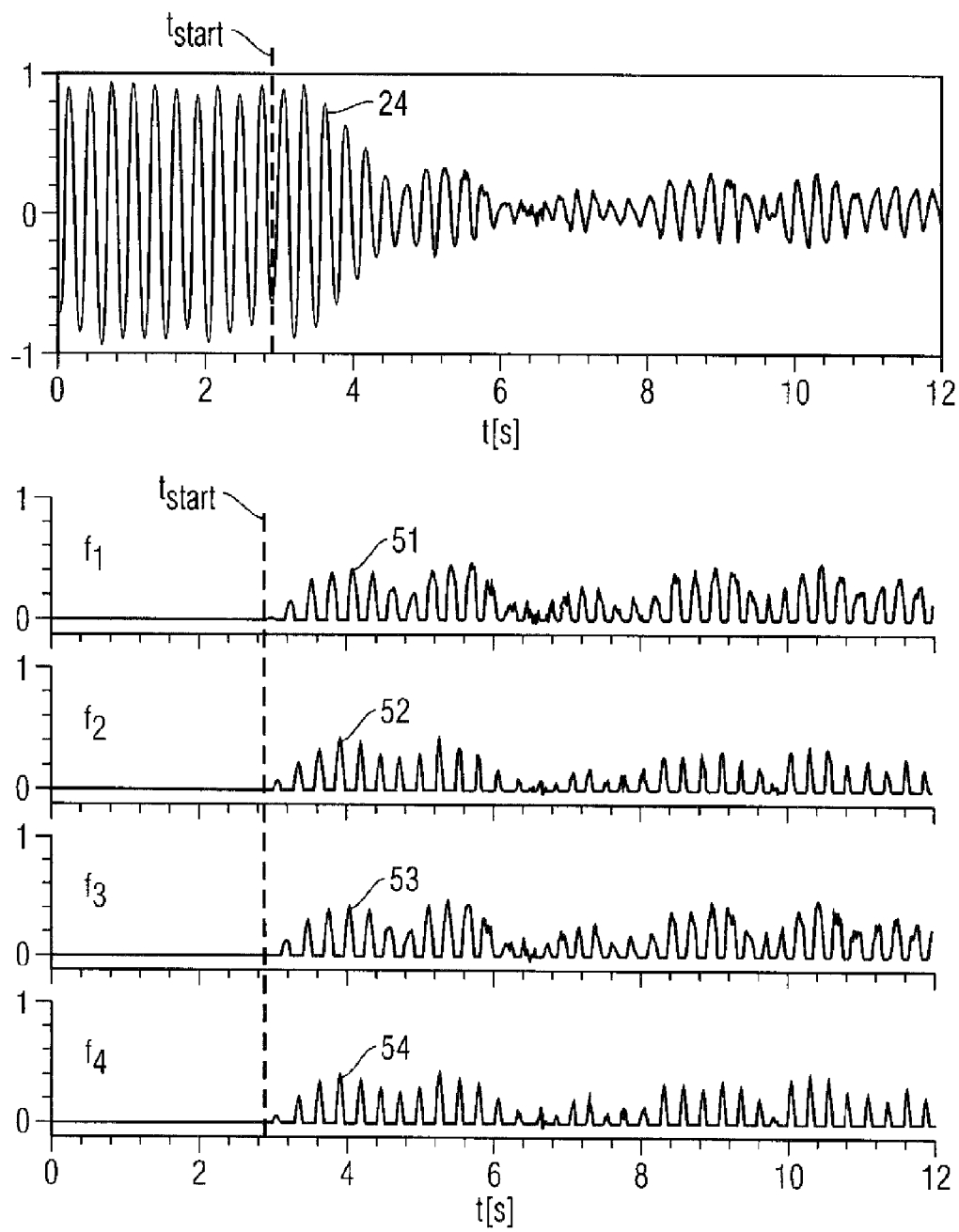
FIG. 14 shows a schematic illustration of a further auditory stimulation method as per an exemplary embodiment.

FIG. 14 illustrates such a stimulation in an exemplary fashion. The modulation signals 51, 52, 53 and 54 have been obtained here from the band-pass filtered measurement signal 24 by means of linear processing steps, by means of which modulation signals the amplitude of frequencies $f_1$ to $f_4$ has been modulated. The control signal 14 has been generated by the superposition of the modulated sinusoidal oscillations, which control signal has been converted into the acoustic stimulation signal 15 by the sound generator 11.

Figure 15A:
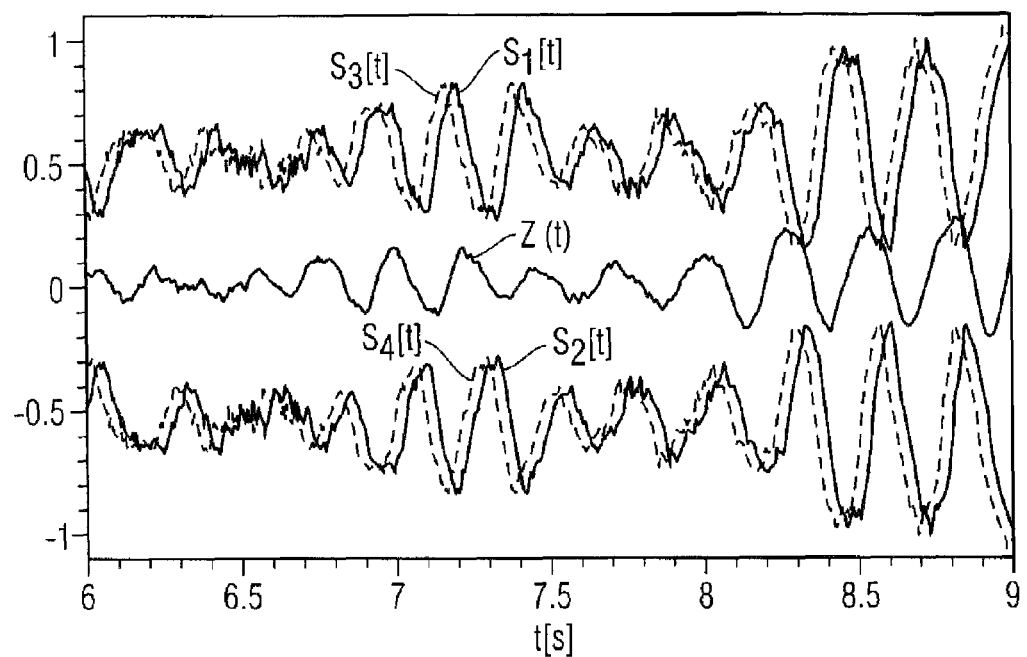
FIGS. 15A and 15B show schematic illustrations of the generation of modulation signals as per an exemplary embodiment.
Figure 15B:
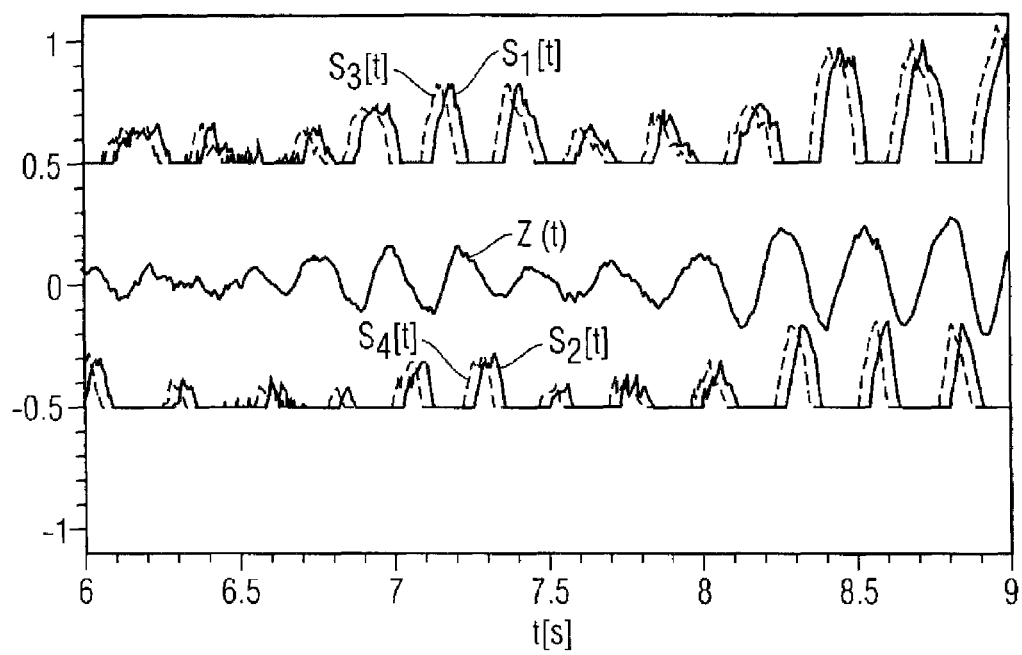

Herein below, FIGS. 15A and 15B are used to explain in an exemplary fashion how the modulation signals 51 to 54 can be obtained from the measurement signal 24. For this, a delay time $\tau$ is first of all fixed, which has been set to be $\tau=T_{stim}/2$ in the present example (other values, such as $\tau=T_{stim}$ or $\tau=3T_{stim}/2$, are likewise possible). By way of example, the frequency $f_{stim}=1/T_{stim}$ can lie in the vicinity of the mean frequency of the measurement signal 24, e.g. in the range between 1 and 30 Hz, more particularly in the range between 5 and 20 Hz. Particular delay times $\tau_1$, $\tau_2$, $\tau_3$ and $\tau_4$ can be calculated for each of the modulation signals 51 to 54 with the aid of the delay time $\tau$, for example with the aid of the following equation:

$$\tau_0 = \tau \cdot \frac{11 - 2 \cdot (j-1)}{8} \quad \text{with } j = 1, 2, 3, 4. \quad (6)$$

By way of example, the modulation signals 51 to 54 can be obtained from the measurement signal 24 by the measurement signal 24 in each case being delayed by the delay times $\tau_1$, $\tau_2$, $\tau_3$ and $\tau_4$:

$$S_j(t) = K \cdot Z(t-\tau_j). \quad (7)$$

In equation (7), $S_1(t)$, $S_2(t)$, $S_3(t)$ and $S_4(t)$ represent the modulation signals 51 to 54 and $Z(t)$ represents the measurement signal 24. K is an amplification factor, which can be selected in a suitable fashion. Furthermore, all negative values (or all values above or below a particular threshold) of the modulation signals $S_1(t)$ to $S_4(t)$ can be set to zero.

According to one refinement illustrated in FIGS. 15A and 15B, the modulation signals $S_1(t)$ to $S_4(t)$ are calculated from only the delay times $\tau_1$ and $\tau_2$, wherein the modulation signals $S_1(t)$ and $S_2(t)$, and $S_3(t)$ and $S_4(t)$ in each case have different polarities:

$$S_1(t) = K \cdot Z(t-\tau_1) \quad (8)$$
$$S_2(t) = -K \cdot Z(t-\tau_1) \quad (9)$$
$$S_3(t) = K \cdot Z(t-\tau_2) \quad (10)$$
$$S_4(t) = -K \cdot Z(t-\tau_2). \quad (11)$$

In FIGS. 15A and 15B the modulation signals $S_1(t)$ and $S_3(t)$ have been displaced upward by a value of 0.5 and the modulation signals $S_2(t)$ and $S_4(t)$ have been displaced downward by a value of 0.5 for the purpose of a clearer illustration.

As shown in FIG. 15B, all negative values (or all values above or below a certain threshold) of the modulation signals $S_1(t)$ to $S_4(t)$ can be set to zero. The generation of the modulation signals 51 to 54 shown in FIG. 14 corresponds to the generation of the modulation signals $S_1(t)$ to $S_4(t)$ shown in FIGS. 15A and 15B. While the foregoing has been described in conjunction with exemplary embodiments, it is understood that the term "exemplary" is merely meant as an example, rather than the best or optimal. Accordingly, the application is intended to cover alternatives, modifications and equivalents, which may be included within the spirit and scope of the disclosure herein.

Additionally, in the preceding detailed description, numerous specific details have been set forth in order to provide a thorough understanding of the present application. However, it should be apparent to one of ordinary skill in the art that the present device and method disclosed herein may be practiced without these specific details. In other instances, well-known methods, procedures, components, and circuits have not been described in detail so as not to unnecessarily obscure aspects of the present application.

The invention claimed is:

1. A device for desynchronizing a patient's neuronal brain activity involving a neuron population firing in a pathologically synchronized manner, the device comprising:
    a stimulation unit configured to generate an acoustic stimulation signal to stimulate the neuron population when the acoustic stimulation signal is aurally received by the patient;
    a measurement unit configured to record a measurement signal on a patient, which measurement signal reproduces the neuronal activity in an auditory cortex of the patient or a region connected thereto; and
    a control unit configured to actuate the stimulation unit based on the measurement signal such that the stimulation unit converts the measurement signal into the acoustic stimulation signal,
    wherein the control unit is further configured to:
        process the measurement signal in a linear or nonlinear fashion,
        modulate amplitudes of a plurality of purely sinusoidal oscillations with the processed measurement signal to generate a plurality of acoustic control stimulation signals that are offset in time from each other, and
        feed the plurality of acoustic control stimulation signals into the stimulation unit to generate a plurality of acoustic stimulation signals offset in time from each other.

2. A device for desynchronizing a patient's neuronal brain activity involving a neuron population firing in a pathologically synchronized manner, the device comprising:

a stimulation unit configured to generate an acoustic stimulation signal to stimulate the neuron population when the acoustic stimulation signal is aurally received by the patient;

a measurement unit configured to record a measurement signal on a patient, which measurement signal reproduces the neuronal activity in an auditory cortex of the patient or a region connected thereto; and a control unit configured to actuate the stimulation unit based on the measurement signal such that the stimulation unit converts the measurement signal into the acoustic stimulation signal, wherein the control unit is further configured to process the measurement signal in a linear or nonlinear fashion, to modulate amplitudes of a plurality of oscillations with the processed measurement signal to generate a plurality of acoustic stimulation signals and to feed the plurality of acoustic stimulation signals into the stimulation unit, wherein the acoustic stimulation signals of the plurality of acoustic stimulation signals are offset in time, and wherein the control unit is further configured to:
process the measurement signal in a linear or nonlinear fashion,
modulate amplitudes of a plurality of oscillations with the processed measurement signal to generate a plurality of acoustic control stimulation signals that are offset in time from each other, and
feed the plurality of acoustic control stimulation signals into the stimulation unit to generate a plurality of acoustic stimulation signals offset in time from each other, and
wherein each of the plurality of oscillations is a frequency mixture.

3. A device for desynchronizing a patient's neuronal brain activity involving a neuron population firing in a pathologically synchronized manner, the device comprising:
a stimulation unit configured to generate an acoustic stimulation signal to stimulate the neuron population when the acoustic stimulation signal is aurally received by the patient;
a measurement unit configured to record a measurement signal on a patient, which measurement signal reproduces the neuronal activity in an auditory cortex of the patient or a region connected thereto; and
a control unit configured to actuate the stimulation unit based on the measurement signal such that the stimulation unit converts the measurement signal into the acoustic stimulation signal,
wherein the control unit is further configured to:
process the measurement signal in a linear or nonlinear fashion,
modulate amplitudes of a plurality of oscillations with the processed measurement signal to generate a plurality of acoustic control stimulation signals that are offset in time from each other, and
feed the plurality of acoustic control stimulation signals into the stimulation unit to generate a plurality of acoustic stimulation signals offset in time from each other, and
wherein the plurality of acoustic stimulation signals are grouped in pairs of acoustic stimulation signals and the acoustic stimulation signals of the same pair have different polarities.

4. The device as claimed in claim 3, wherein the acoustic stimulation signals of the same pair have the same offset in time.

5. A device for desynchronizing a patient's neuronal brain activity involving a neuron population firing in a pathologically synchronized manner, the device comprising:
a stimulation unit configured to generate an acoustic stimulation signal to stimulate the neuron population when the acoustic stimulation signal is aurally received by the patient;
a measurement unit configured to record a measurement signal on a patient, which measurement signal reproduces the neuronal activity in an auditory cortex of the patient or a region connected thereto; and
a control unit configured to actuate the stimulation unit based on the measurement signal such that the stimulation unit converts the measurement signal into the acoustic stimulation signal,
wherein the control unit is further configured to:
process the measurement signal in a linear or nonlinear fashion,
modulate amplitudes of a plurality of oscillations with the processed measurement signal to generate a plurality of acoustic control stimulation signals that are offset in time from each other, and
feed the plurality of acoustic control stimulation signals into the stimulation unit to generate a plurality of acoustic stimulation signals offset in time from each other, and
wherein the amplitudes of N oscillations are modulated with the processed measurement signal to generate the plurality of acoustic stimulation signals, wherein the amplitude of the jth of the N oscillations is modulated with a processed measurement signal $S_j(t)$ represented by the following equation:

$$S_j(t) = K \cdot Z(t - \tau_j) \text{ with } j = 1, \ldots, N,$$

wherein K is an amplification factor, $Z(t)$ is the measurement signal and $\tau_j$ is a delay time.

6. A device for desynchronizing a patient's neuronal brain activity involving a neuron population firing in a pathologically synchronized manner, the device comprising:
a stimulation unit configured to generate an acoustic stimulation signal to stimulate the neuron population when the acoustic stimulation signal is aurally received by the patient;
a measurement unit configured to record a measurement signal on a patient, which measurement signal reproduces the neuronal activity in an auditory cortex of the patient or a region connected thereto; and
a control unit configured to actuate the stimulation unit based on the measurement signal such that the stimulation unit converts the measurement signal into the acoustic stimulation signal,
wherein the control unit is further configured to:
process the measurement signal in a linear or nonlinear fashion,
modulate amplitudes of a plurality of oscillations with the processed measurement signal to generate a plurality of acoustic control stimulation signals that are offset in time from each other, and
feed the plurality of acoustic control stimulation signals into the stimulation unit to generate a plurality of acoustic stimulation signals offset in time from each other, and
wherein only a part of the processed measurement signal lying above or below a prescribed threshold is used for the amplitude modulation.

7. A method for desynchronizing a patient's neuronal brain activity involving a neuron population firing in a pathologically synchronized manner, the method comprising:
- recording a measurement signal on a patient, which measurement signal reproduces the neuronal activity in an auditory cortex of the patient or a region connected thereto;
- processing the measurement signal in a linear or nonlinear fashion;
- modulating amplitudes of a plurality of oscillations with the processed measurement signal to generate a plurality of acoustic stimulation signals; and
- generating the plurality of acoustic stimulation signals to stimulate the neuron population when the plurality of acoustic stimulation signal is aurally received by the patient, wherein the acoustic stimulation signals of the plurality of acoustic stimulation signals are offset in time,
- wherein each of the plurality of oscillations is a pure sinusoidal oscillation.

8. A method for desynchronizing a patient's neuronal brain activity involving a neuron population firing in a pathologically synchronized manner, the method comprising:
- recording a measurement signal on a patient, which measurement signal reproduces the neuronal activity in an auditory cortex of the patient or a region connected thereto;
- processing the measurement signal in a linear or nonlinear fashion;
- modulating amplitudes of a plurality of oscillations with the processed measurement signal to generate a plurality of acoustic stimulation signals; and
- generating the plurality of acoustic stimulation signals to stimulate the neuron population when the plurality of acoustic stimulation signal is aurally received by the patient, wherein the acoustic stimulation signals of the plurality of acoustic stimulation signals are offset in time,
- wherein each of the plurality of oscillations is a frequency mixture.

9. A method for desynchronizing a patient's neuronal brain activity involving a neuron population firing in a pathologically synchronized manner, the method comprising:
- recording a measurement signal on a patient, which measurement signal reproduces the neuronal activity in an auditory cortex of the patient or a region connected thereto;
- processing the measurement signal in a linear or nonlinear fashion;
- modulating amplitudes of a plurality of oscillations with the processed measurement signal to generate a plurality of acoustic stimulation signals; and
- generating the plurality of acoustic stimulation signals to stimulate the neuron population when the plurality of acoustic stimulation signal is aurally received by the patient, wherein the acoustic stimulation signals of the plurality of acoustic stimulation signals are offset in time,
- wherein the plurality of acoustic stimulation signals are grouped in pairs of acoustic stimulation signals and the acoustic stimulation signals of the same pair have different polarities.

10. The method as claimed in claim 9, wherein the acoustic stimulation signals of the same pair have the same offset in time.

11. A method for desynchronizing a patient's neuronal brain activity involving a neuron population firing in a pathologically synchronized manner, the method comprising:
- recording a measurement signal on a patient, which measurement signal reproduces the neuronal activity in an auditory cortex of the patient or a region connected thereto;
- processing the measurement signal in a linear or nonlinear fashion;
- modulating amplitudes of a plurality of oscillations with the processed measurement signal to generate a plurality of acoustic stimulation signals; and
- generating the plurality of acoustic stimulation signals to stimulate the neuron population when the plurality of acoustic stimulation signal is aurally received by the patient, wherein the acoustic stimulation signals of the plurality of acoustic stimulation signals are offset in time,
- wherein the amplitudes of N oscillations are modulated with the processed measurement signal to generate a plurality of acoustic stimulation signals, wherein the amplitude of the jth of the N oscillations is modulated with a processed measurement signal $S_j(t)$ represented by the following equation:

$$S_j(t) = K \cdot Z(t-\tau_j) \text{ with } j=1, \ldots, N,$$

wherein K is an amplification factor, $Z(t)$ is the measurement signal and $\tau_j$ is a delay time.

12. A method for desynchronizing a patient's neuronal brain activity involving a neuron population firing in a pathologically synchronized manner, the method comprising:
- recording a measurement signal on a patient, which measurement signal reproduces the neuronal activity in an auditory cortex of the patient or a region connected thereto;
- processing the measurement signal in a linear or nonlinear fashion;
- modulating amplitudes of a plurality of oscillations with the processed measurement signal to generate a plurality of acoustic stimulation signals; and
- generating the plurality of acoustic stimulation signals to stimulate the neuron population when the plurality of acoustic stimulation signal is aurally received by the patient, wherein the acoustic stimulation signals of the plurality of acoustic stimulation signals are offset in time,
- wherein only a part of the processed measurement signal lying above or below a prescribed threshold is used for the amplitude modulation.

* * * * *